US012472352B2

(12) United States Patent
Sánchez Jaime

(10) Patent No.: US 12,472,352 B2
(45) Date of Patent: Nov. 18, 2025

(54) METHODS AND SYSTEMS FOR TREATMENT OF SKIN OF A SUBJECT

(71) Applicant: HIGH TECHNOLOGY PRODUCTS, S.L.U., Barcelona (ES)

(72) Inventor: José Antonio Sánchez Jaime, Barcelona (ES)

(73) Assignee: HIGH TECHNOLOGY PRODUCTS, S.L.U., Barcelona (ES)

( * ) Notice: Subject to any disclaimer, the term of this patent is extended or adjusted under 35 U.S.C. 154(b) by 863 days.

(21) Appl. No.: 17/499,266

(22) Filed: Oct. 12, 2021

(65) Prior Publication Data

US 2022/0023622 A1 Jan. 27, 2022

Related U.S. Application Data

(63) Continuation of application No. PCT/EP2020/060261, filed on Apr. 9, 2020.

(30) Foreign Application Priority Data

Apr. 11, 2019 (EP) .................................... 19382277

(51) Int. Cl.

| | |
|---|---|
| ***A61N 1/06*** | (2006.01) |
| ***A61N 1/08*** | (2006.01) |
| ***A61N 1/32*** | (2006.01) |
| ***A61N 1/40*** | (2006.01) |

(52) U.S. Cl.

CPC ................. *A61N 1/06* (2013.01); *A61N 1/08* (2013.01); *A61N 1/403* (2013.01); *A61N 1/328* (2013.01)

(58) Field of Classification Search

CPC . A61N 1/06; A61N 1/08; A61N 1/403; A61N 1/328; A61N 1/322; A61N 1/40;

(Continued)

(56) References Cited

U.S. PATENT DOCUMENTS

2008/0167585 A1* 7/2008 Khen ....................... A61N 7/00 601/6

2008/0183252 A1* 7/2008 Khen ..................... A61B 18/14 607/101

(Continued)

FOREIGN PATENT DOCUMENTS

EP 2258332 A1 12/2010

JP S5463580 A 5/1979

(Continued)

OTHER PUBLICATIONS

International Search Report in PCT/EP2020/060261, mailed Jul. 9, 2020, 3 pages.

(Continued)

*Primary Examiner* — Adam Z Minchella

*Assistant Examiner* — Ashleigh Lauren Kern

(74) *Attorney, Agent, or Firm* — Edell, Shapiro & Finnan, LLC

(57) ABSTRACT

An apparatus for treatment of a skin of a subject is provided. The apparatus comprises a base, an applicator head which is rotatably mounted with respect to the base around an axis of rotation, and defines a cavity for receiving a portion of the skin of the subject, a drive for rotating the applicator head, and a pump for reducing a pressure in the cavity for sucking the portion of the skin of the subject into the cavity. The applicator head further comprises one or more electrodes, and the apparatus further comprises one or more electrical power sources and a control system for controlling electrical energy supply to the electrodes. A cross-section of the cavity with a plane comprising the axis of rotation is non-constant in rotation. Also disclosed are methods for treatment of the skin.

20 Claims, 12 Drawing Sheets

(58) Field of Classification Search
CPC .............. A61F 2007/0095; A61F 7/007; A61F 2007/0052; A61B 2017/00026; A61B 2017/00084; A61H 2007/009; A61H 2201/10; A61H 2201/1215; A61H 2201/1671; A61H 2201/5002; A61H 2201/5005; A61H 7/008; A61H 2201/1207; A61H 2201/1635; A61H 2201/1654; A61H 2201/50; A61H 2201/5082
See application file for complete search history.

(56) References Cited

U.S. PATENT DOCUMENTS

| | | | | |
|---|---|---|---|---|
| 2010/0312157 A1* | 12/2010 | Yan | A61H 7/008 | 601/112 |
| 2015/0265492 A1* | 9/2015 | Eckhouse | A61N 5/025 | 606/42 |

FOREIGN PATENT DOCUMENTS

| | | | | |
|---|---|---|---|---|
| JP | 2005528935 A | 9/2005 | | |
| JP | 2011045610 A | 3/2011 | | |
| KR | 101768177 B1 * | 8/2017 | | A61H 7/008 |
| WO | 2011162174 A1 | 12/2011 | | |

OTHER PUBLICATIONS

Japanese Office Action with English translation, Application No. 2021559311, Aug. 13, 2024, 8 pages.
Chinese Office Action with English translation, Application No. 202080026585.8, Aug. 6, 2024, 17 pages.
Chinese Office Action with English translation, Application No. 202080026585.8, Apr. 3, 2024 30 pages.

* cited by examiner

METHODS AND SYSTEMS FOR TREATMENT OF SKIN OF A SUBJECT

CROSS-REFERENCE TO RELATED APPLICATIONS

This application relates to and claims the benefit and priority to International Application No. PCT/EP2020/060261, filed Apr. 9, 2020, which claims the benefit and priority to European Application No. EP19382277.2 filed on Apr. 11, 2019.

FIELD

The present disclosure relates to methods and systems for treatment of skin of a subject. The present disclosure more particularly relates to methods and systems for treatment of skin of a subject involving applying electromagnetic energy, particularly RF energy, to the skin and substantially simultaneously massaging a portion of the skin.

BACKGROUND

The aesthetic treatment of radiofrequency (RF) on the skin induces an electric current that circulates through the treated tissue. The term radiofrequency (or "RF") generally refers to an alternating current at high frequencies. The oscillation frequency may be e.g. 0.1-10 MHz.

The resistance offered by the (skin) tissue to the passage of the current produces the transformation of RF energy into thermal energy. The transformation of electric current to thermal energy depends on different factors related to the characteristics of the treated tissue, as well as the characteristics of the RF (such as the power and frequency) selected for the treatment.

Cosmetic effects that have been associated with an RF treatment include skin tightening and a local reduction of adipose tissue, i.e. fat. The treatments may be generally be regarded as cosmetic rather than therapeutic.

On the other hand, mechanical massage is known to affect the subcutaneous connective tissue and dermis by promoting blood flow and releasing muscle tension and pain, thereby stimulating the release of toxins from the skin. Mechanical massage improves microcirculation and facilitates the drainage of trapped intracellular fluid from the lymphatic system.

Skin treatment devices are known that aim to combine an RF treatment with a massage. For example, U.S. Pat. No. 8,435,194 discloses such a device including an annular massage head encircling and rotating around the RF applicator. U.S. Pat. No. 6,662,054 discloses deforming the skin so that a region of the skin protrudes from surrounding skin, and applying RF energy to the skin.

KR 101 678 177 B1 discloses a cup for a skin massage, which comprises the following: a cup member connected to a suction unit and having a suction space with a negative pressure formed therein; a rotary massage member which rotates inside the cup member by a motor, and includes a protruding unit for pressuring the skin of a user for a massage. The protruding unit for a massage is arranged separately from a rotational axis of the motor, moves in circle on a plane while pressurizing the skin projected by the negative pressure generated inside the suction space, and evenly massages the skin, thereby remarkably improving a recovery effect on skin tissues after a skin treatment procedure.

US 2008/183252 discloses medical or aesthetic devices for treating cellulite by combining mechanical and electrical energy. The device uses pressure on the tissue and/or induces heat into the treated tissue. The pressure may be provided on the tissue by a rotatable treatment member, which may be spring-loaded to exert pressure on the tissue. The heat may be induced by RF energy provided by electrodes. The RF electrodes may be combined with the rotatable treatment members.

JP 2011 045610 discloses a biological stimulation device. Permanent magnets are provided as rotatable magnetic stimulation means as well as fixed electrical stimulation electrode.

EP 2 258 332 A1 discloses a massage apparatus comprising a drive unit and a rotatable head coupled to the drive unit for rotation about an axis, and a rotatable head for use with such a massage device. The rotatable head has a skin-engaging end face to contact skin to be massaged. The massage apparatus is configured such that the skin-engaging end face lies in a plane substantially perpendicular to the axis of rotation of the rotatable head.

There still exists a need for devices which can provide a more effective treatment of the skin.

SUMMARY

In a first aspect, an apparatus for treatment of a skin of a subject is provided. The apparatus comprises a base, an applicator head which is rotatably mounted with respect to the base around an axis of rotation, and the applicator head defines a cavity for receiving a portion of the skin of the subject. The apparatus further comprises a drive for rotating the applicator head, and a pump for reducing a pressure in the cavity for sucking the portion of the skin of the subject into the cavity. The applicator head further comprises one or more electrodes, and the apparatus further comprises one or more electrical power sources and a control system for controlling electrical energy supply to the first and second electrodes. A cross-section of the cavity with a plane including the axis of rotation is non-constant in rotation.

In accordance with this aspect, an apparatus for the treatment of a skin of a subject is provided that combines an effective massage with an RF treatment. An increased massaging effect is established because of the cavity in which a vacuum or negative pressure is created. A portion of the skin thus is sucked into the cavity.

A negative pressure or vacuum in any of the herein disclosed methods and systems may be regarded as a negative pressure of 0.6-1 atm, and specifically a negative pressure of 0.7-0.98 atm. I.e. the pressure in the cavity, when in use may particularly be in the range of 0.02-0.3 atm (20-270 mbar).

The cavity rotates and has a non-constant cross-section in rotation. This means that the portion of the skin inside the cavity is successively compressed and stretched due to rotation of the cavity. A cross-section of the cavity being non-constant with the same plane in rotation may also be understood as the cross-section of the cavity being non-constant through different planes (defining angles between them) comprising the axis of rotation.

The negative pressure applied to the skin also improves or ensures the contact between the skin and RF electrodes. This can reduce local burns of the skin.

Electromagnetic energy, particularly RF energy, is applied to the skin at the same time. Due to the skin being sucked into the cavity the RF treatment can reach deeper lying tissue. Moreover, the rotation of the applicator head ensures that continuously differing areas of a skin portion receive the RF energy. Heat is thus applied more homogeneously to the skin portion in the cavity and burns can thus effectively be avoided or at least reduced.

A cross-section of the cavity with a plane including the axis of rotation being non-constant in rotation may be interpreted herein to mean that the bottom or sidewalls of the cavity are irregular to such an extent that the skin is effectively massaged. The irregularity may be created by protrusions or recesses in the bottom or sidewalls and in these cases, they must be dimensioned such that the skin is effectively sucked into a recess or pushed away by a protrusion. I.e. the protrusions or recesses may have a height or depth of at least 0.2 and specifically at least 0.5 cm. The irregularity may also be created by some form of undulation or non-circularity of the border of the cavity. Because the skin is forced into a recess and out of a recess in rotation, massaging takes place. Similarly, in rotation the skin may be forced around a protrusion or projection, massaging takes place. And similarly, if the sidewalls substantially irregular, specifically, non-circular, a skin fold encounters a changing width of the cavity in rotation and is successively compressed and stretched to provide a massaging effect.

Recesses in the bottom of the cavity may also be used to collect some gel, lotion, cream, or lubricant that may have been applied to a subject's skin to reduce friction with the apparatus before starting the treatment.

Particularly a temporary reduction in width or space in rotation provides a pinching effect, which can locally and temporarily reduce blood flow, which can make the treatment more effective.

In a second aspect, a method for treatment of a skin of a subject is provided. The method comprises applying a negative pressure to a portion of the skin such that the portion of skin is sucked into a cavity which is rotatable around an axis of rotation, and wherein a cross-section of the cavity with a plane through the axis of rotation is non-constant in rotation. The method furthermore comprises massaging the portion of the skin by rotating the cavity, and applying RF energy to the skin.

The methods may be particularly cosmetic, i.e. non therapeutic. Non-therapeutic as used herein implies that the methods do not aim or achieve the curing of a disease or malfunction of the body. Rather, these cosmetic methods provide a localized effect of skin tightening or reduction of fat tissue.

In some examples, a first electrode and a second electrode may be provided, the second electrode being arranged at a substantially diametrically opposite position of the cavity to the first electrode. In other examples, only a single electrode may be provided.

Within the scope of the present disclosure, unipolar, monopolar, bipolar and multipolar (i.e. tripolar, tetrapolar, octipolar) RF treatments may be used. With monopolar or unipolar treatments, a single electrode is provided which continuously changes polarity. The other electrode is passive (it does not receive an alternating positive and negative polarity) and may be carried by the subject itself, generally relatively far removed from the electrode of the RF apparatus. As an example, if the RF apparatus issued for a treatment of a subject's abdomen, a second electrode may be carried by the subject on his/her back.

In bipolar treatments, two electrodes are provided with continuously changing opposed polarity so that the electric current flows from one electrode to the other and in the opposite direction. The treatment achieved with such an arrangement may be more superficial than with a monopolar arrangement. Multipolar arrangements are also known, in which three, four or more electrodes are provided. Typically, the plus and minus of these electrodes are controlled to create pairs of electrodes acting as a positive and a negative.

In some examples, four electrodes may be arranged in or around the cavity. Pairs of these electrodes may be switched on and off intermittently. At any moment, one pair of electrodes is active, and the other pair of electrodes is not.

A professional will in accordance with his/her preferences and experience be able to choose between different arrangements suitable for different treatments. This may be adapted in accordance with the objective of the treatment but also as a function of a subject's preference.

Prior to such a treatment, an area of the body of the subject may be prepared by providing a lotion, cream, or lubricant on the skin to reduce friction with the apparatus. Areas of the body that may be treated using the methods and apparatus disclosed herein include e.g. lower or higher abdomen, flanks, thighs, buttocks, "banana rolls", arms and other.

In some examples, a border of the cavity may be non-circular. The cavity may thus have a non-circular cross-section. For example, an elliptical border of the cavity may effectively provide a massaging effect by a varying width of the cross-section of the cavity as the cavity rotates. The cavity may in these examples be elliptical in cross-section along most of the depth of the cavity. In other examples, the cross-section may be substantially rectangular or square, specifically with rounded corners.

In some examples, the border of the cavity may include a first undulated edge and optionally a second undulated edge. A non-constant cross-section may however be established in a variety of ways using recesses and/or protrusions or projections in the edges, the sidewall(s) and/or bottom of the cavity.

In some examples, the electrodes may be arranged at least partially within the cavity. In other examples, the electrodes may be arranged outside the cavity.

In some examples, the applicator head may be configured to rotate more than 360°, and particularly may be configured to rotate continuously. An aspect of having a continuous (i.e. uninterrupted) rotation is that a local peak of heat that may cause a burn can be avoided.

In some examples, the cavity may comprise a centrally arranged protuberance. Depending on the levels of vacuum applied, it has been found beneficial to have a centrally arranged protuberance that avoids a skin fold getting stuck in the cavity and thus allows for a smoother and less painful rotation of the applicator head. In some examples, a varying level of pressure may be used in the cavity with the same objective. Specifically, the pressure/vacuum may be applied in a pulsed manner.

DESCRIPTION OF THE DRAWINGS

Non-limiting examples of the present disclosure will be described in the following, with reference to the appended drawings, in which.

DETAILED DESCRIPTION

Figure 1A:
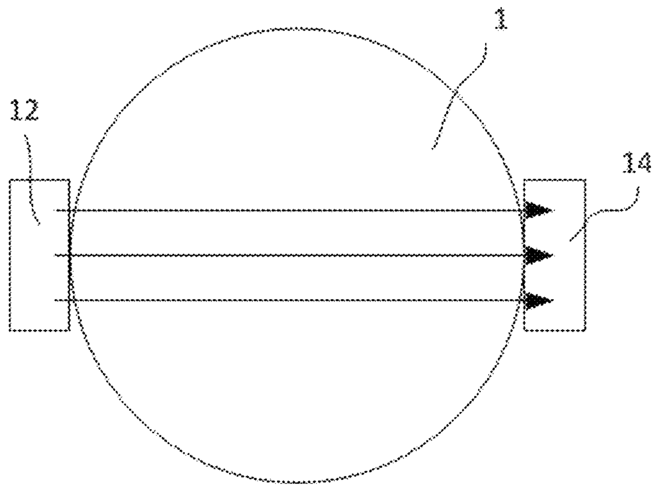
FIGS. 1A-1G are schematic illustrations of various technical concepts that are applied in methods and systems according to the present disclosure.

FIGS. 1A-1G are schematic illustrations of various technical concepts that are applied in methods and systems according to the present disclosure. FIG. 1A very schematically illustrates an area of treatment 1. The area of treatment may be constituted by a cavity. A vacuum may be applied to such a cavity, such that when it is placed onto the skin of a subject, a portion of the skin protrudes with respect to the rest of the skin and enters into the cavity.

Also schematically illustrated are a first electrode 12 and a second electrode 14. The second electrode 14 may typically be arranged diametrically opposite to the first electrode 12. At any moment, one of the electrodes will have a positive polarity and the other of the electrodes will have a negative polarity. In the instance depicted in FIG. 1A, the electrode 12 is positive while the electrode 14 is negative. Current thus flows from electrode 12 to electrode 14. This current encounters resistance from the skin and other tissue of the subject. The electrical energy can thus be converted into thermal energy i.e. heat. Such a heat treatment has been linked to several aesthetically pleasing effects on the skin and area of the body being treated.

The electrical currents find the shortest route, or the route of least resistance from the first electrode 12 to the second electrode 14. The tissue that is arranged between the two electrodes will thus receive more heat than the tissue that is somewhat displaced from the centre. As heat is concentrated in a portion of the tissue, local burns could occur. It is known for a professional, e.g. a nurse or physician to continuously move the applicator over the skin of a subject so as to avoid such burns. This is however not entirely reliable and moreover means a significant physical exercise for the person handling the applicator.

Figure 1B:
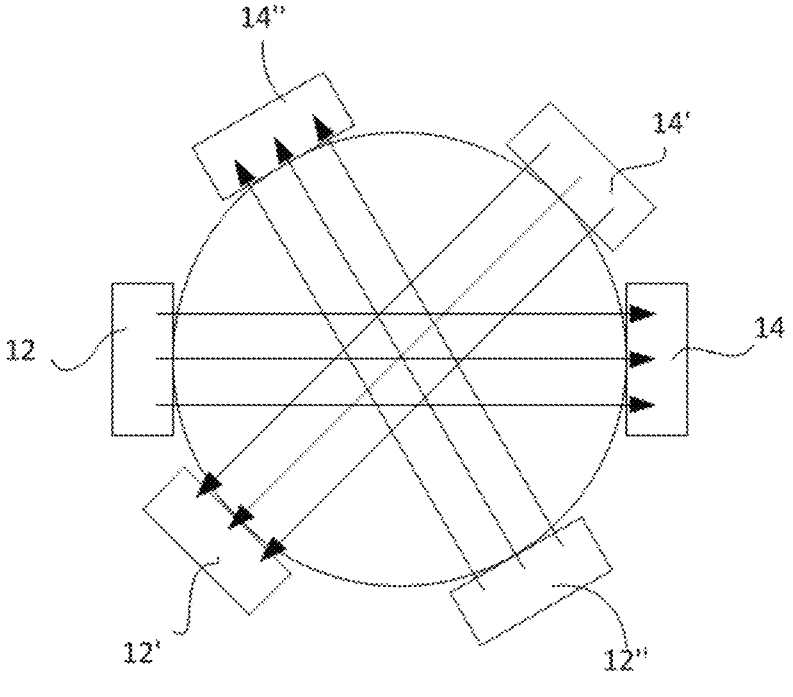

FIG. 1B illustrates an improvement that is provided by having an applicator head that is rotatable with respect to a (handheld) base. By rotating the applicator head, the relative positions of the electrodes 12 and 14 with respect to a portion of the skin will change. Only two such other positions are schematically illustrated in FIG. 1B. Thus, the electrical currents will be distributed more homogeneously throughout the area to be treated and the heat will be distributed more homogeneously as well. A drive for rotating the applicator head may include e.g. a motor and may be powered by battery or through a connection to the electrical grid.

Homogeneous heat distribution may thus be achieved without excessive physical strain to a person overseeing the treatment. For the avoidance of doubt, it is noted that a person in charge of the treatment may hold the RF apparatus and move the apparatus over a region of the body of the subject. This movement is in addition to the rotational movement of the applicator head.

Figure 1C:
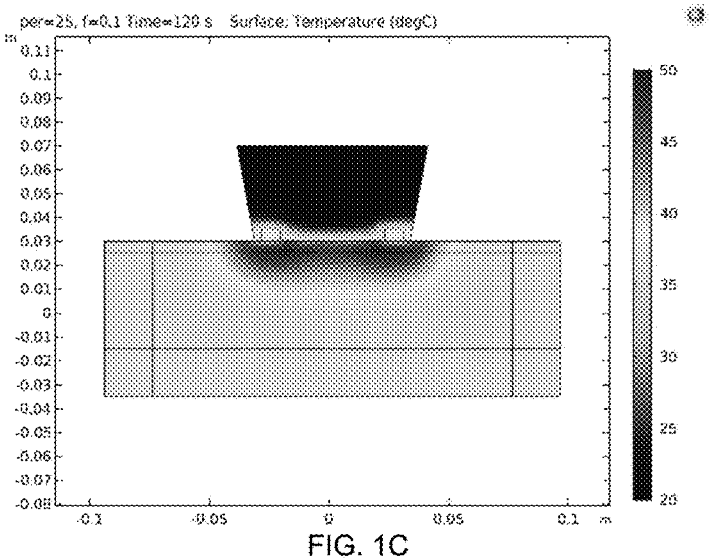
Figure 1D:
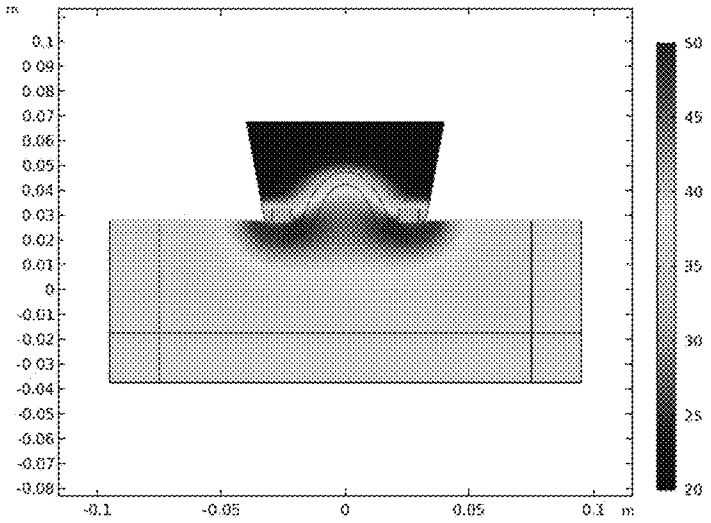

FIGS. 1C and 1D schematically illustrate the difference in heat distribution in the presence (FIG. 1D) and absence (FIG. 1C) of a vacuum in the cavity. In FIG. 1D it may be recognized that when using a vacuum, a portion of the skin is sucked in and the heat will reach deeper lying tissue than in the absence of a vacuum. A skin treatment may thus become more effective for these deeper lying tissues.

Figure 1E:
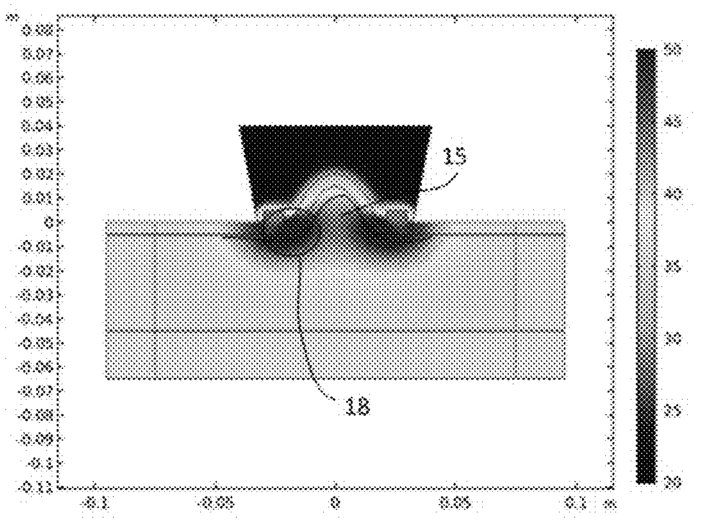

A comparison between FIGS. 1D and 1E serves to illustrate that the heat distribution is more homogeneous when the cavity is in rotation (FIG. 1D) than when it is not (FIG. 1E). In FIG. 1E, two hot spots 18 have been indicated. These "hot spots" 18 are portions of the skin fold 15 that are sucked into or towards cavity that accumulate a relatively large amount of heat.

Figure 1F:
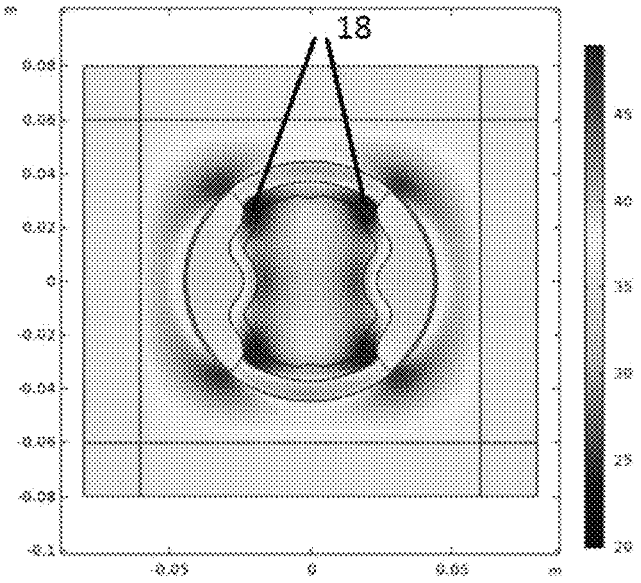
Figure 1G:
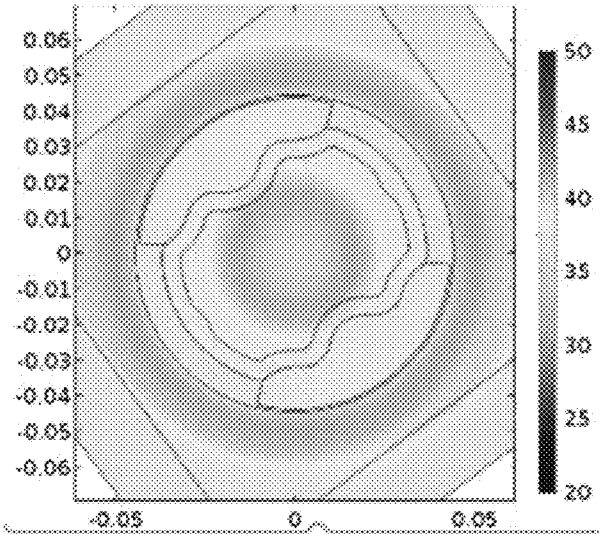

The same may be seen in the simulated heat distributions in FIGS. 1F and 1G using an applicator head that will be illustrated in FIG. 2. In FIG. 1F, hot spots 18, may be identified. These cannot be found in the simulation of FIG. 1G. It is noted that these effects are found regardless of the frequency of the RF and that the electrical power applied is constant in the different simulations. Simulations were carried out for RF frequencies between 0.1 and 1 MHz. The rotational speed in the simulations was 0.25 cycles/s.

Figure 2A:
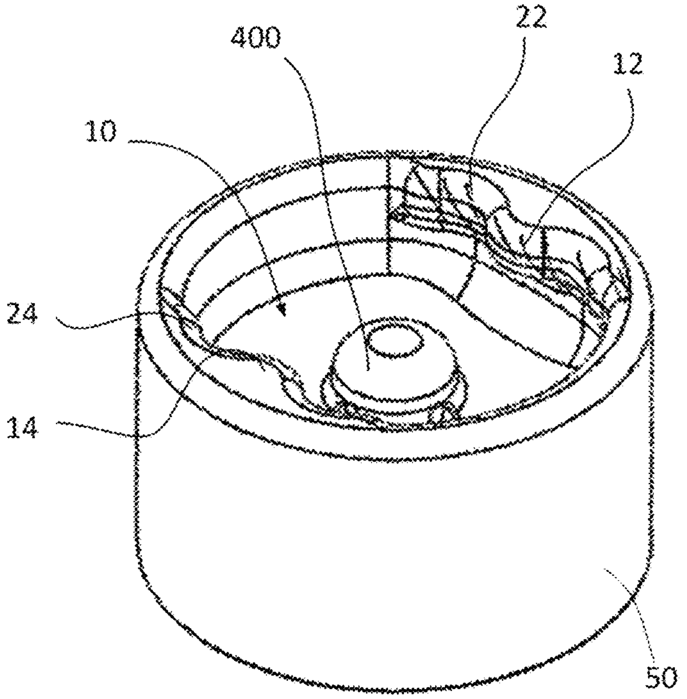
FIGS. 2A-2E are schematic illustrations of various examples of an applicator head.

FIGS. 2A-2D are schematic illustrations of various examples of an applicator head. In FIG. 2A, an applicator head 50 with a cavity 10 is shown. A central protrusion or projection 400 is provided in the cavity. Two diametrically opposite undulated side edges 22 and 24 may be seen.

The provision of undulated edges 22 and 24 with respect to an otherwise circular cross-section means that the cross-section of the cavity with a plane comprising the axis of rotation 11 is non-constant. This may also readily be seen in FIG. 2B. A skin fold inside the cavity will encounter continuously increasing and decreasing width of the cavity and will thus be massaged more effectively. The combination of a vacuum with the massaging or pinching effect can reduce blood flow locally and thereby make the treatment more effective.

Figure 2B:
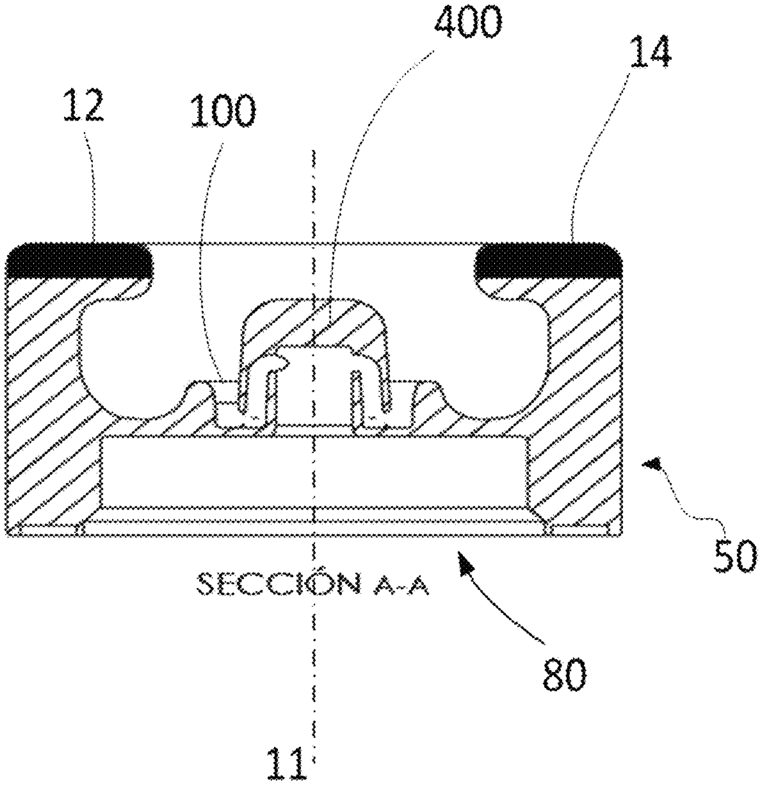

With reference to the cross-sectional view of FIG. 2B, the applicator head 50 has a female coupling 80 by which it can be coupled to a base. Vacuum ports 100 are arranged in the bottom of the cavity. First electrode 12 and second electrode 14 may be arranged on diametrically opposite sides of the cavity. In particular, they may be arranged on both undulated edges, as indicated in FIG. 2A.

Figure 2C:
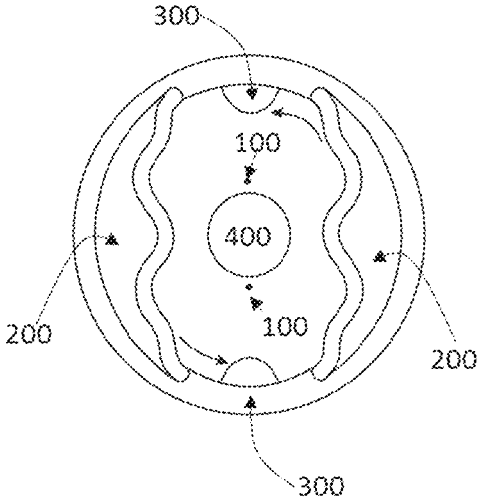

FIG. 2C provides a top view of the same example of the applicator head.

The central protrusion 400 in this example avoids that a skin fold is sucked into the cavity to such an extent that it gets stuck inside the cavity. In rotation, such a situation can be painful. With such a central protrusion a relatively high level of vacuum may be applied constantly. In the absence of such a protrusion, a lower level of vacuum could be applied, or a varying pressure level e.g. pulsed could be used. Such a pulsed pressure variation may provide for an additional massage effect. Such a pulsation may be performed e.g. at a frequency of 1-20 Hz.

The protrusion 400 in this example is a cylinder with a rounded top. In another non-illustrated example, such a protrusion 400 in the bottom of the cavity may be eccentrically positioned i.e. not coinciding with the axis of rotation. This can achieve the same effect of avoiding disproportionate sucking of a portion of the skin into the cavity and can increase irregularity of the cavity in rotation.

FIG. 2C illustrates a top view of a different example, in which there are additional inwardly protruding bulges 300 between the undulating sidewalls. These bulges 300 increase the massaging or pinching effect of the skin that has been previously explained.

Figure 2E:
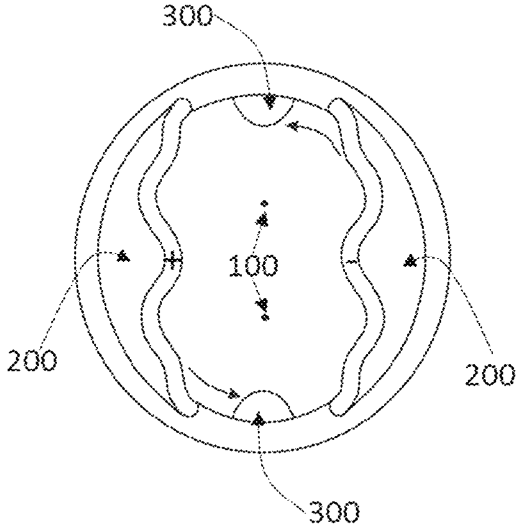
Figure 2D:
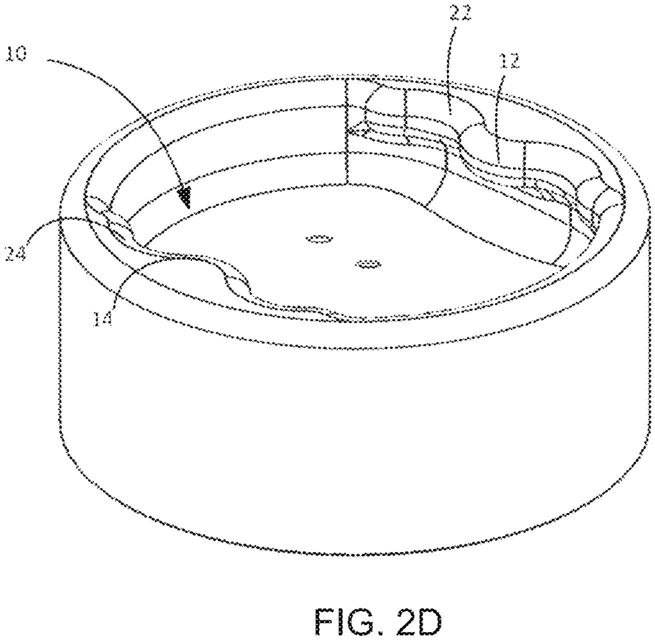

FIGS. 2D and 2E illustrate an isometric view and a top view of yet a further example, in which there is no protrusion centrally arranged on the bottom of the cavity. In these cases, the vacuum level may be varied or pulsed as described before.

Figure 3A:
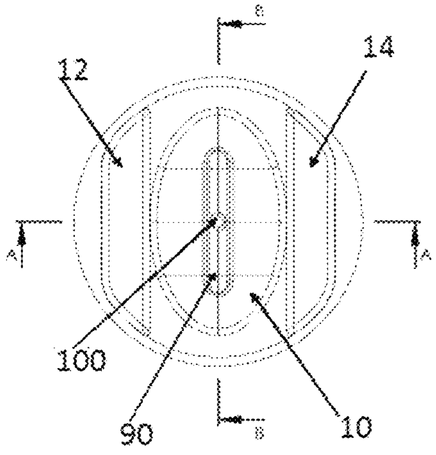
FIGS. 3A-3C are schematic illustrations of another example of an applicator head.
Figure 3B:
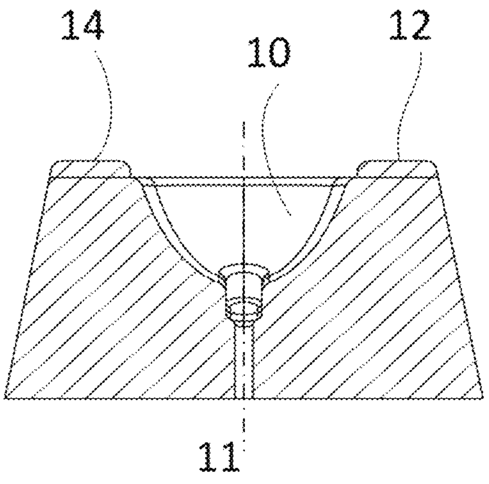
Figure 3C:
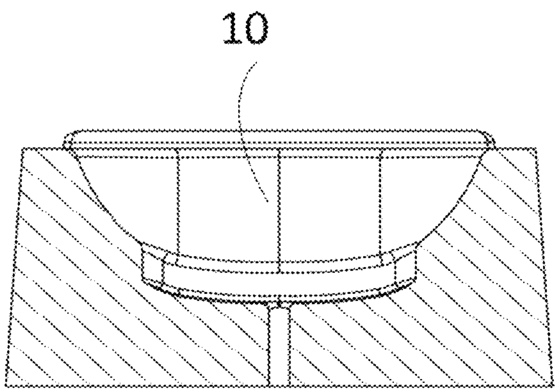

FIGS. 3A-3C are schematic illustrations of another example of an applicator head. In the example of FIG. 3, the cavity 10 has an elliptical cross section as seen in a top view. The electrodes 12 and 14 are arranged diametrically opposite to each other with respect to cavity 10. In the example of FIG. 3, a centrally arranged recess 90 in the bottom of the cavity is provided. The port 100 to which the suction or vacuum mechanism is connected is arranged centrally in recess 90.

Recess 90 may have a depth of at least 0.2 cm, a width of at least 0.5 cm and a length of at least 1.5 cm. In a specific example, the recess may have a depth of e.g. 0.2-1 cm and a width of 0.5-2 cm. The length may e.g. be of 4-9 cm. The dimensions of the recess may be chosen such that the recess 90 is large enough that skin can enter into the recess 90. Again, this increases the aforementioned massaging or pinching effect.

FIG. 3B shows a cross-section of the cavity 10 with a plane comprising the axis of rotation. After rotation of 90°, the cross-section of the cavity 10 with the same plane is shown in FIG. 3C. As may be readily seen in FIGS. 3B and 3C, the elliptical cross-section means that the width of the cavity in cross-section with a plane through the axis of rotation varies as the cavity rotates.

Figure 4A:
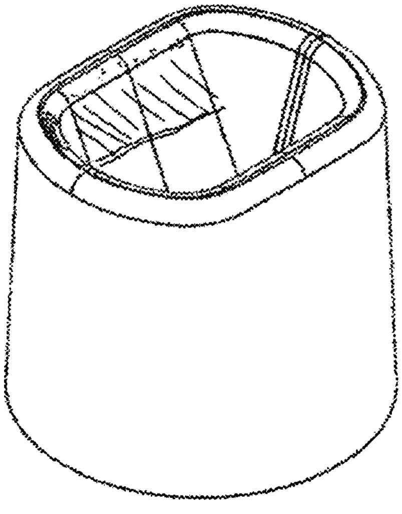
FIGS. 4A-4D are schematic illustrations of yet another example of an applicator head.
Figure 4B:
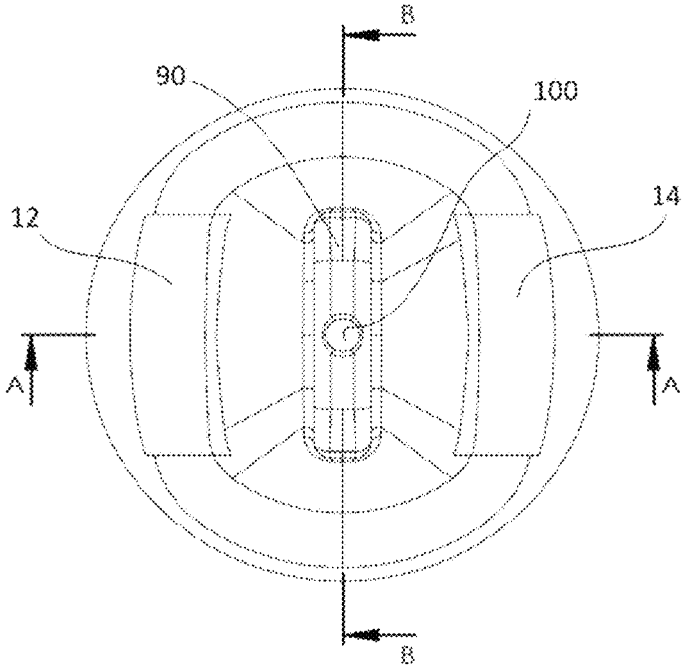
Figure 4C:
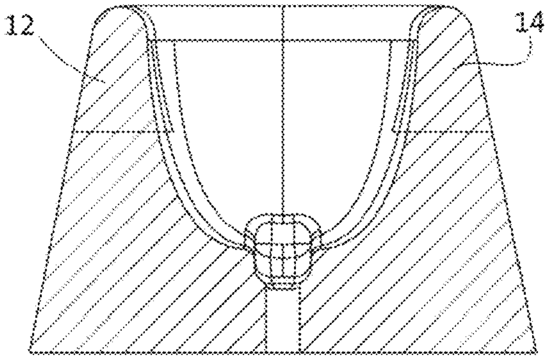
Figure 4D:
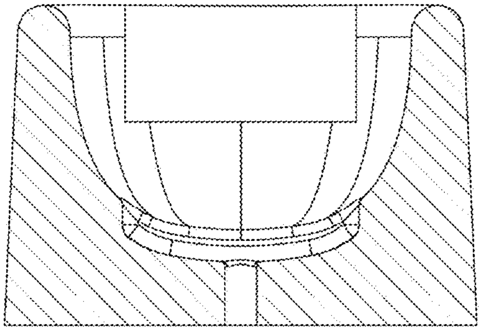

FIGS. 4A-4D are schematic illustrations of yet another example of an applicator head. FIG. 4A shows an isometric view, FIG. 4B shows a top view and FIGS. 4C and 4D show two cross-sectional views. The applicator head of FIG. 4 is generally comparable to the applicator head illustrated in FIG. 3. One difference is that in FIG. 4, the electrodes 12 and 14 are partially arranged inside the cavity. In FIG. 3, the electrodes are arranged outside the cavity.

The cavity in the example of FIG. 4 is also deeper, with steeper sidewalls than in the example of FIG. 3.

Figure 5:
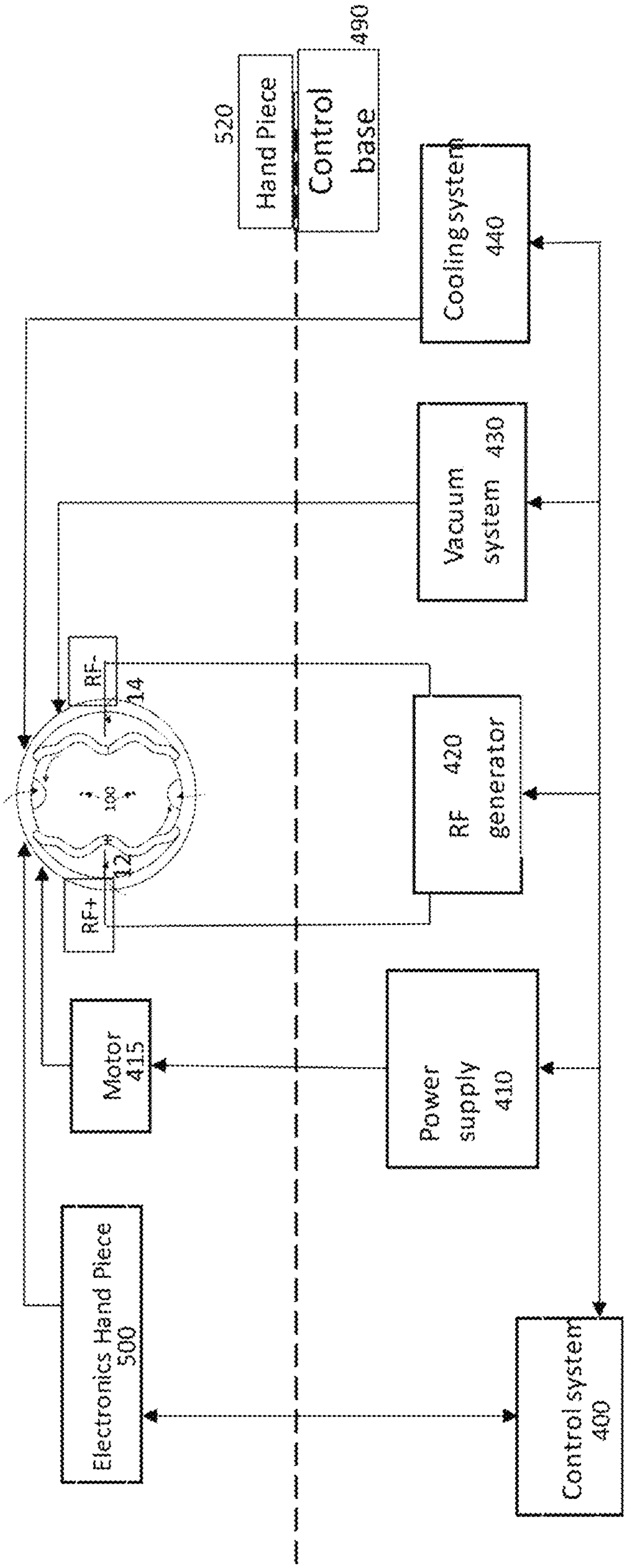
FIG. 5 schematically illustrates an example of a control system that may be used in various examples.

FIG. 5 schematically illustrates an example of a control system that may be used in various examples. An apparatus for applying a treatment to the skin may include a control unit or base 490 and a handheld applicator 520 (see also FIG. 6). The control unit may include e.g. a pump for applying the vacuum, and may include the power supply and may further include an RF generator. The handheld piece may be connected to the control unit via a flexible tube. The flexible tube can provide electric, electronic and pneumatic connection between the control unit and the handheld applicator.

As illustrated in FIG. 5, the handheld applicator may include electronics 500, a motor 415 and the RF electrodes 12 and 14. The handheld applicator in some examples may include e.g. a display, optionally a tactile display, and may include various control buttons, switches and slides for setting e.g. a negative pressure to be applied to the cavity, the RF frequency and power, the rotational speed and the duration of treatment. In some examples, a user may select a treatment from a plurality of predefined treatments. For each of these predefined treatments, settings including power, frequency, speed, duration and others may have been pre-programmed.

In examples of the methods, the apparatus may be configured to continuously rotate the applicator head in the same direction. Some prior art devices apply a partial rotation e.g. 180 degrees and then rotates back. However, if the rotation is interrupted, at the moment of standstill a local peak of heat may be produced. This can be avoided by having the applicator head rotate continuously. This has been further illustrated with respect to FIGS. 8A and 8B.

In these figures, simulations of heat production and resulting skin temperature of an applicator having a cavity with two electrodes that are in diametrically opposite locations with respect to the cavity are shown. The simulation parameters were as follows: rotational velocity of 16.5 RPM, RF voltage 300 V, and RF frequency 0.5 MHz.

Figure 8A:
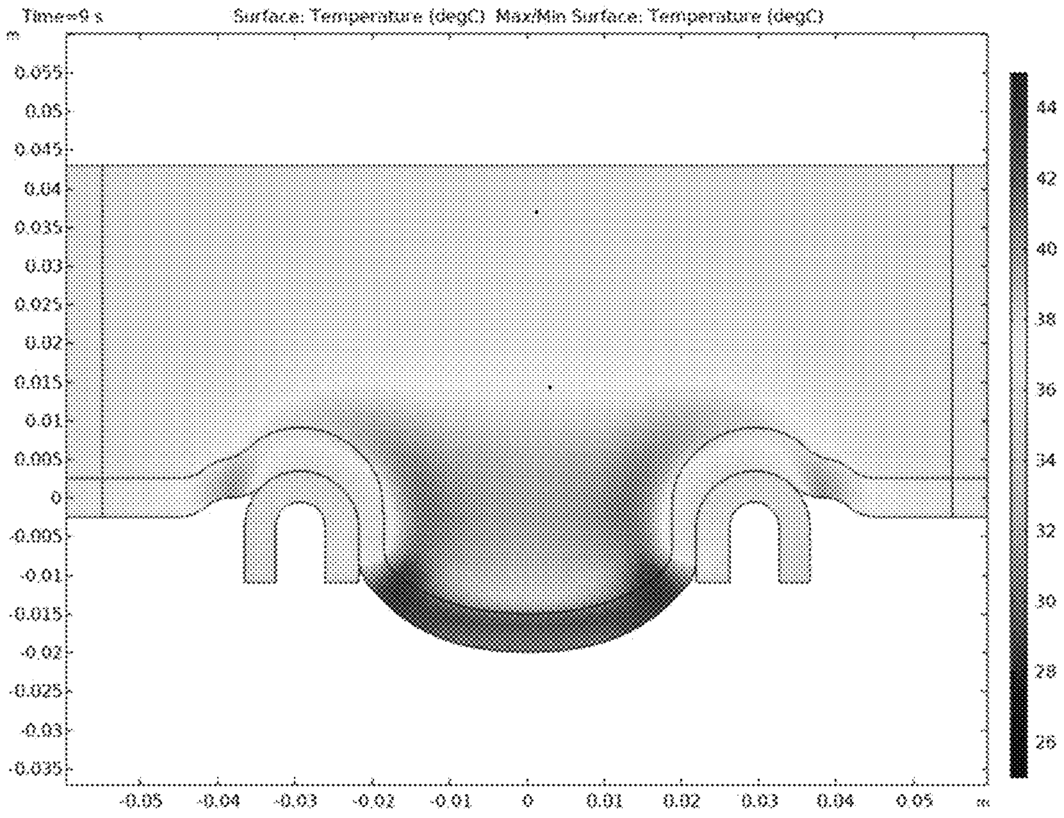
FIGS. 8A and 8B schematically illustrate the effect on local skin temperature in continuous versus interrupted rotation of an applicator head.
Figure 8B:
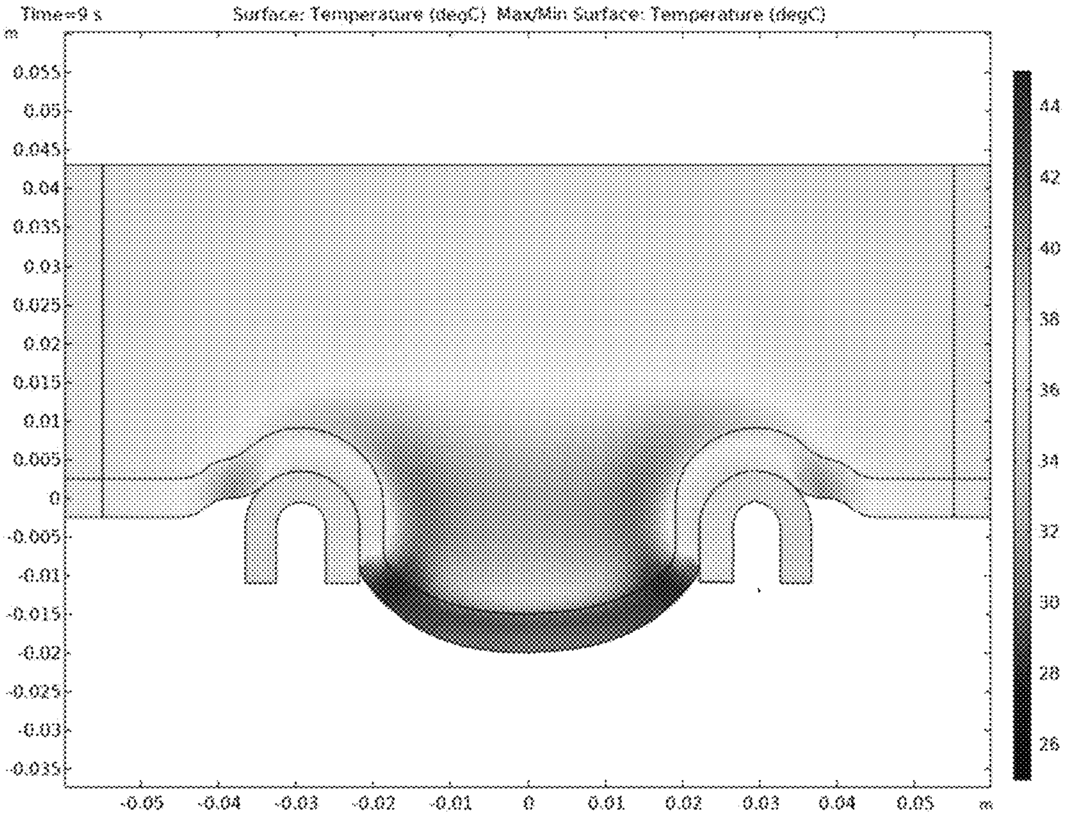

In FIG. 8A, a result is shown for an applicator that is in continuous rotation, i.e. the cavity (and the electrodes) rotates at a substantially constant speed in the same direction of rotation. In FIG. 8B, a result is shown for the same applicator, the same voltage on the electrodes, and the same rotational speed. The only difference is that in FIG. 8B, the applicator rotates 180° in one direction, then stops very briefly and rotates in the opposite direction. In this simulation, if the applicator stays in the same position on the skin for as little as 10 seconds (this means that a professional moving the applicator during the treatment of e.g. 30 minutes keeps his/her hand in the same position for only 10 seconds), a hot spot can occur with a skin temperature higher than in the situation of FIG. 8A.

For an effective treatment, the skin temperature objective is generally close to 43° C. This is a threshold temperature at which a skin burn might appear. So, an increase of only one or a few degrees can be significant. With a continuous rotation, the skin temperature is more predictable, and the treatment can be effective (and maintained close to a temperature threshold) and more secure. With an oscillatory motion, either the risk of a burn is increased or the overall temperature of the treatment is reduced.

It is clear that the effect on skin temperature will depend on the shape of the cavity, the speed of rotation, the RF voltage and other treatment parameters. Nonetheless, it can be seen that a continuous rotation in the same direction can be advantageous.

In some examples, part or all of the controls may be incorporated in the control unit, instead of the handheld applicator.

In accordance with the example of FIG. 5, the control unit may include a power supply 410 (e.g. connection with the electrical grid), the RF generator 420, the pump and control of the vacuum system 430 and, optionally a cooling system 440. The cooling system may be used to cool the cavity in case that (over)heating is detected.

The handheld applicator may include electronics 500 as discussed before, a motor 415 for driving the rotation of the applicator head with respect to the base. An overall control system 400 may receive and send control signals to the various subsystems.

Figure 6A:
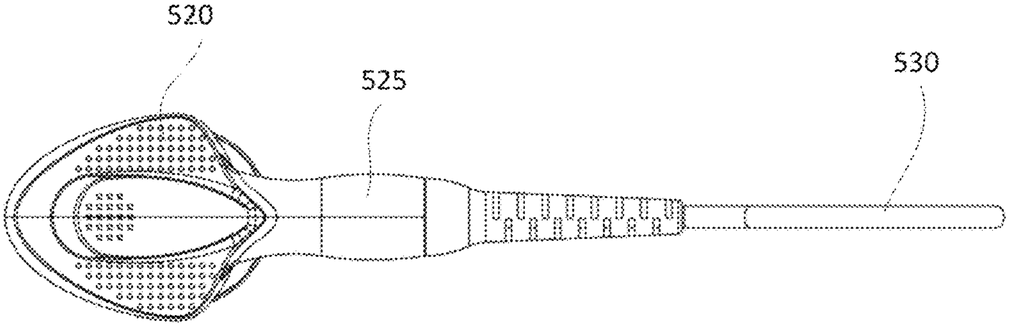
FIGS. 6A and 6B schematically illustrate an example of an applicator head mounted to a base.
Figure 6B:
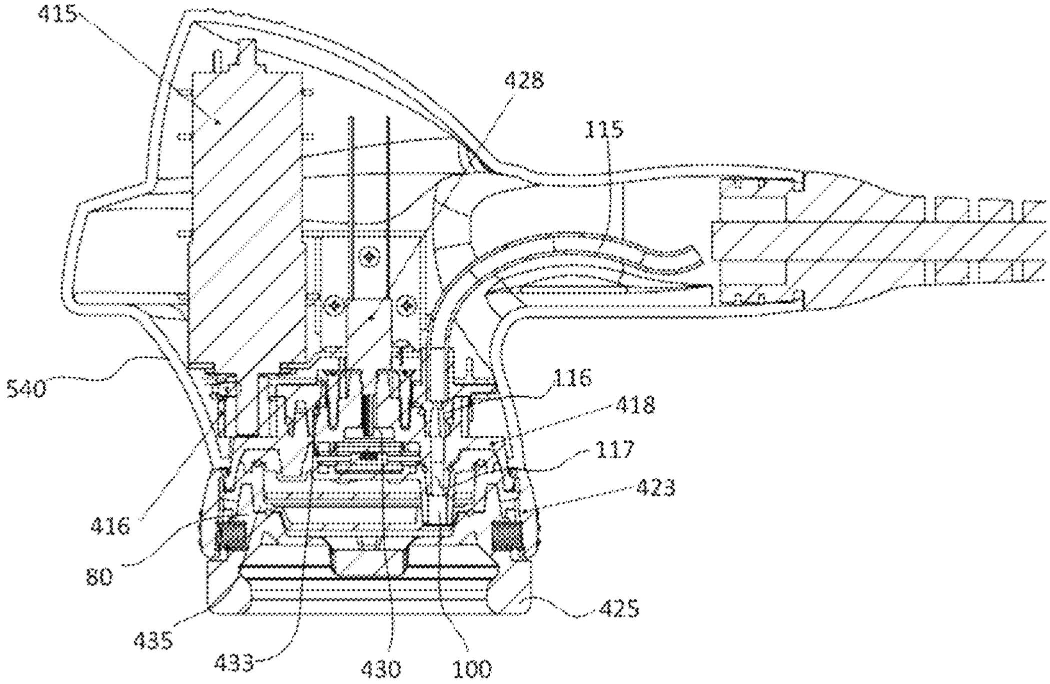

FIGS. 6A and 6B schematically illustrate an example of an applicator head mounted to a base. As shown in FIG. 6A, the handheld applicator 520 may include a handle 525 for holding and manipulating the handheld applicator 520. The handheld applicator 520 may be connected through a flexible tube 530 to a non-illustrated control unit.

The applicator 520 of this example includes a static base 540. The applicator head 425 is rotatably mounted with respect to static base 540. The base 540 may include a motor 415 with a shaft carrying a pinion 416. The pinion in this example is arranged to mesh with a geared ring 418. When the motor is operating, the geared ring 418 can rotate with respect to static base 540. A suitable bearing 433 may be provided for this purpose.

The geared ring 418 may carry a male coupling 435 that is arranged to engage with female coupling 80 of the cavity.

A pneumatic conduit 115 can connect a pump to the applicator head. The conduit 115 ends in a fixed pneumatic connection 116. The pneumatic connection 116 is connected to a ring shaped cavity 117. As the applicator head rotates, the suction port 100 will vary its position along the ring shaped cavity 117 but any position, suction can be applied to the cavity. Suitable O-rings may be provided between different components to ensure control over the vacuum.

The applicator head may further comprise a clamp 423 that supports the rotatable portion of the applicator head. An electrical connection is provided between rotatable part 430 and static part 428. The static part may be connected with electrical power sources in the control unit. Control logic may be provided either in the applicator head (either the static or the rotatable part) or in the control unit to control the power and frequency of the RF energy.

The rotatable part may electrically connect the electrical power source with the electrodes. For example, slip rings, brushes etc. may be used for such a rotatable electrical connection.

Figure 7A:
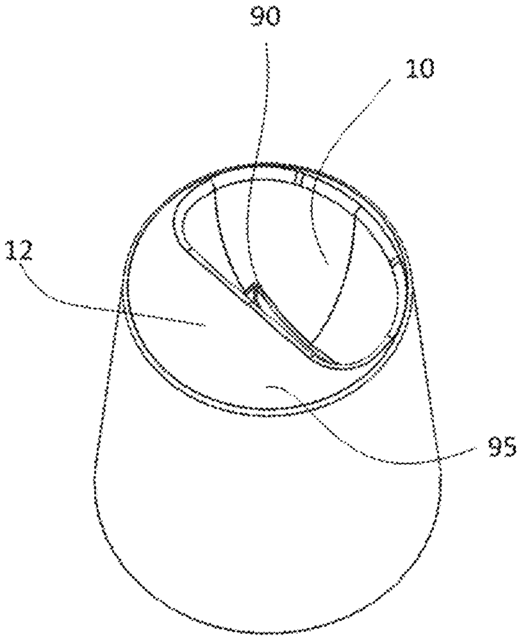
FIGS. 7A-7F schematically illustrate further examples of applicator heads.
Figure 7B:
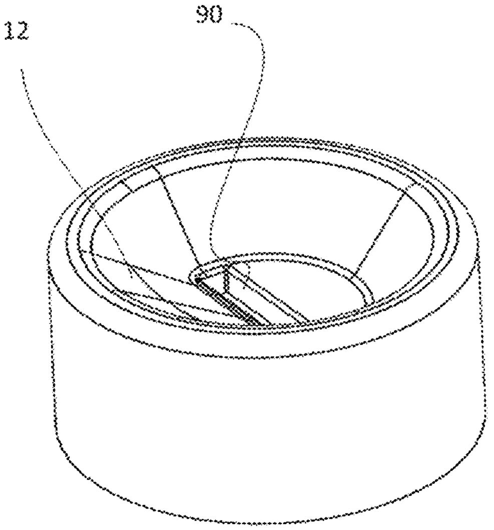

FIGS. 7A and 7B schematically illustrate two further examples of applicator heads. In the example of FIG. 7A, the cavity 10 is eccentrically arranged with respect to applicator head. The cavity 10 may be semi-circular. An electrode 12 may be arranged on an inclined plane 95 of the applicator head. This particular example may be used in a monopolar treatment. The cavity 90 in this example also includes the aforementioned recess 90 with one or more suction ports.

In the example of FIG. 7B, the cavity 10 is part semi-circular whereas the other half of the cavity has a flat inclined sidewall. On this flat (portion of the) sidewall, an electrode 12 may be arranged. Also, these cavities have a cross-section that is non-constant in rotation.

Figure 7C:
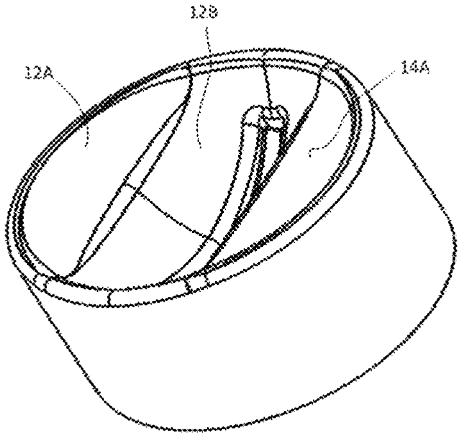
Figure 7D:
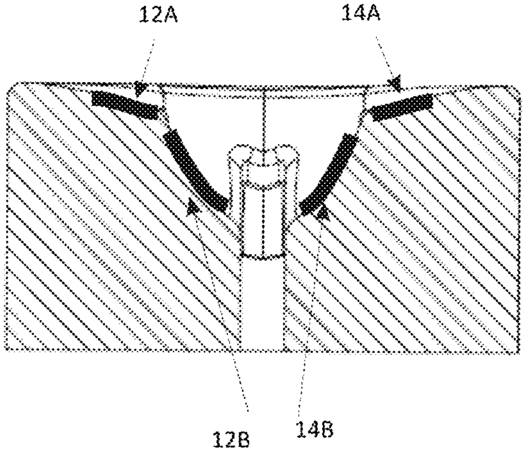

FIGS. 7C and 7D disclose an example of an applicator head comprising four electrodes. The electrodes may be configured in pairs, a first pair 12A, 14A and a second pair 12B, 14B. The pairs of electrodes are activated intermittently such that at any time, only a single pair of electrodes is active. For example, the first pair 12A and 14A may form a positive and a negative pole. The central portion of the cavity in these examples may have a substantially elliptical cross-section.

Figure 7E:
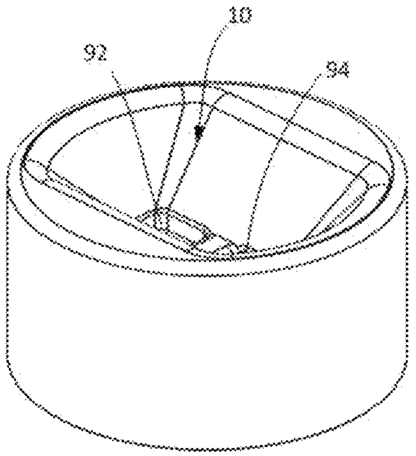
Figure 7F:
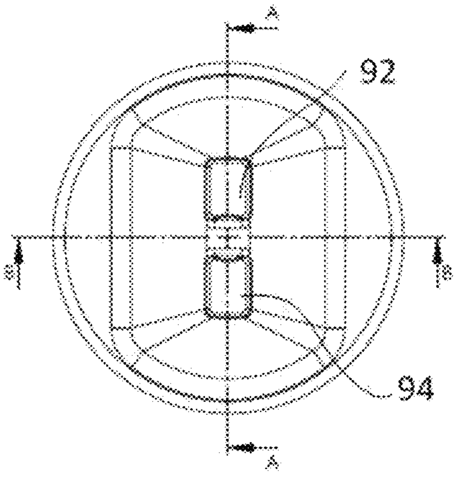

FIGS. 7E and 7F schematically illustrate an isometric view and a top view of a further example of an applicator head. The applicator head is generally similar to the example of FIG. 4. However, recess 90 in this example has been substituted by two smaller recesses 92 and 94. The recesses 92 and 94 may have a length of approximately 1.5 cm, a depth of at least 0.2 cm, and a width of at least 0.5 cm and a length of at least 1.5 cm. In a specific example, the recess may have a depth of e.g. 0.2-1 cm and a width of 0.5-2 cm.

In any of the examples disclosed herein, the cavity may be made from an electrically insulating material, e.g. a polymer such as polypropylene or thermoplastic elastomers (thermoplastic rubbers). The thermoplastic rubbers may be a mixture of different materials. The electrodes in any of the examples described herein may be made from a variety of materials. Examples include stainless steel and aluminum. The electrodes may be coated with a layer of anodized aluminum of any other semiconductor material.

Although not shown in any of the examples herein disclosed, any of the applicator heads may be provided with a lubricant deposit and a mechanism for selectively releasing a lubricant. And any of the applicator heads may include some form of skin measurement device, e.g. a thermal sensor or impedance sensor to measure the temperature of the skin. Such a skin temperature measurement or indication may be used in the control of the power of the RF and may be used also to interrupt the treatment should an inadvertent rise of temperature occur.

For reasons of completeness, a number of aspects of the present disclosure are set out in the following numbered clauses:

Clause 1. An apparatus for treatment of a skin of a subject comprising a base, an applicator head which is rotatably mounted with respect to the base around an axis of rotation, and defines a cavity for receiving a portion of the skin of the subject, a drive for rotating the applicator head, and a pump for reducing a pressure in the cavity for sucking the portion of the skin of the subject into the cavity, wherein the applicator head further comprises one or more electrodes, and the apparatus further comprises one or more electrical power sources and a control system for controlling electrical energy supply to the electrodes, and wherein a cross-section of the cavity with a plane including the axis of rotation is non-constant in rotation.

Clause 2. The apparatus according to clause 1, comprising a first electrode and a second electrode, the second electrode being arranged at a substantially diametrically opposite position of the cavity to the first electrode.

Clause 3. The apparatus according to clause 1, including only a single electrode.

Clause 4. The apparatus according to clause 1, wherein a border of the cavity is non-circular.

Clause 5. The apparatus according to clause 4, wherein the border of the cavity includes a first undulated edge.

Clause 6. The apparatus according to clause 5, wherein the border of the cavity includes a second undulated edge.

Clause 7. The apparatus according to clause 4, wherein the border of the cavity is substantially elliptical.

Clause 8. The apparatus according to any of clauses 1-7, wherein the electrodes are arranged at least partially within the cavity.

Clause 9. The apparatus according to any of clauses 1-7, wherein the electrodes are arranged outside the cavity.

Clause 10. The apparatus according to any of clauses 1-9, further comprising a drive control for controlling the drive.

Clause 11. The apparatus according to clause 10, wherein the applicator head is configured to rotate more than 360°.

Clause 12. The apparatus according to clause 10 and 11, wherein the applicator head is configured to rotate continuously.

Clause 13. The apparatus according to any of clauses 1-12, wherein the cavity comprises protuberance inside the cavity.

Clause 14. The apparatus according to clause 13, wherein the protuberance is arranged centrally inside the cavity.

Clause 15. The apparatus according to clause 13, wherein the protuberance is arranged eccentrically inside the cavity.

Clause 16. The apparatus according to any of clauses 1-15, wherein a bottom of the cavity comprises one or more recesses configured to receive a portion of skin.

Clause 17. The apparatus according to any of clauses 1-16, wherein the applicator head further comprises a sensor for sensing a temperature of the skin.

Clause 18. The apparatus according to any of clauses 1-17, further comprising a handle for holding the base.

Clause 19. The apparatus according to any of clauses 1-18, wherein the applicator head further comprises a lubricant reservoir, and one or more lubricant supply conduits for delivering lubricant to the skin of the subject.

Clause 20. A method for treatment of a skin of a subject, comprising applying a negative pressure to a portion of the skin such that the portion of skin is sucked into a cavity which is rotatable around an axis of rotation, and wherein a cross-section of the cavity with a plane through the axis of rotation is non-constant in rotation, massaging the portion of the skin by rotating the cavity, and applying electromagnetic energy to the skin.

Clause 21. The method according to clause 20, comprising rotating the cavity with a varying speed of rotation.

Clause 22. The method according to clause 20 or 21, wherein the negative pressure is varied.

Clause 23. The method according to clause 22, wherein the negative pressure is pulsed.

Clause 24. The method according to any of clauses 21-23, comprising rotating the cavity continuously.

Clause 25. The method according to any of clauses 21-24, wherein the electromagnetic energy is RF energy.

Clause 26. The method according to clause 25, wherein RF energy is applied to the skin with a single electrode.

Clause 27. The method according to clause 25, wherein RF energy is applied to the skin through two electrodes of opposing polarity.

Clause 28. The method according to any of clauses 21-27, wherein the method is non-therapeutic.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

What is claimed is:

1. An apparatus for treatment of a skin of a subject comprising a base;

an applicator head which is rotatably mounted with respect to the base around an axis of rotation, and defines a cavity for receiving a portion of the skin of the subject, and wherein the applicator head is configured to rotate more than 360 degrees; and is configured to rotate continuously in one direction, a drive coupled to the applicator head and configured to continuously rotate the applicator head in the one direction; and a pump for reducing a pressure in the cavity for sucking the portion of the skin of the subject into the cavity;

the applicator head further comprises one or more electrodes configured to apply electromagnetic energy to the portion of the skin of the subject, and the apparatus further comprises one or more electrical power sources and a control system for controlling electrical energy supply to the electrodes, the electromagnetic energy being RF energy; and wherein a cross-section of the cavity with a plane including the axis of rotation is non-constant in rotation.

2. The apparatus according to claim 1, wherein the one or more electrodes include a first electrode and a second electrode, the second electrode being arranged diametrically opposite position of the cavity to the first electrode.

3. The apparatus according to claim 1, wherein the applicator includes only a single electrode.

4. The apparatus according to claim 1, wherein a border of the cavity is non-circular and wherein the one or more electrodes include a first electrode and a second electrode, the second electrode being arranged diametrically opposite position of the cavity to the first electrode, and wherein the first electrode and the second electrode are arranged completely within the cavity at a distance from the border.

5. The apparatus according to claim 1, wherein the border of the cavity includes one or more undulated edges.

6. The apparatus according to claim 1, wherein the one or more electrodes are arranged at least partially within the cavity.

7. The apparatus according to claim 1, wherein the one or more electrodes are arranged outside the cavity.

8. The apparatus according to claim 1, further comprising a protuberance inside the cavity.

9. The apparatus according to claim 8, wherein the protuberance is arranged centrally inside the cavity.

10. The apparatus according to claim 8, wherein the protuberance is arranged eccentrically inside the cavity.

11. The apparatus according to claim 1, wherein a bottom of the cavity comprises one or more recesses configured to receive a portion of skin.

12. The apparatus according to claim 1, wherein the applicator head further comprises a sensor for sensing a temperature of the skin.

13. The apparatus according to claim 1, further comprising a handle for holding the base.

14. The apparatus according to claim 1 wherein the applicator head further comprises a lubricant reservoir, and one or more lubricant supply conduits for delivering lubricant to the skin of the subject.

15. The apparatus according to claim 1, wherein the applicator head is configured to rotate at a variable speed.

16. The apparatus according to claim 4, wherein the border of the cavity is elliptical.

17. The apparatus according to claim 1, wherein the border of the cavity includes a first undulated edge located on a first side of the cavity and a second undulated edge located on a second side of the cavity opposite the first side of the cavity.

18. The apparatus according to claim 17, wherein the applicator head further comprises a bulge located between the first and second undulating edges.

19. The apparatus according to claim 11, wherein the one or more recesses comprise one or more suction ports.

20. The apparatus according to claim 17, wherein the one or more electrodes include only a first electrode and a second electrode, and wherein the first electrode is arranged on the first undulated edge, and the second electrode is arranged on the second undulated edge.

* * * * *